(12) United States Patent  
Engelhardt

(10) Patent No.: US 6,603,553 B1  
(45) Date of Patent: Aug. 5, 2003

(54) ARRANGEMENT FOR DETECTING FLUORESCENT LIGHT FROM A PLURALITY OF SAMPLE POINTS

(75) Inventor: Johann Engelhardt, Bad Schonborn (DE)

(73) Assignee: Leica Microsystems Heidelberg GmbH, Mannheim (DE)

( * ) Notice: Subject to any disclaimer, the term of this patent is extended or adjusted under 35 U.S.C. 154(b) by 237 days.

(21) Appl. No.: 09/681,109

(22) Filed: Jan. 10, 2001

(30) Foreign Application Priority Data

Jan. 28, 2000 (DE) .......................... 100 03 754

(51) Int. Cl.[7] ............................................. G01N 21/64
(52) U.S. Cl. .................................... 356/417; 250/458.1
(58) Field of Search ...................... 356/417; 250/458.1, 250/459.1, 461.1, 461.2

(56) References Cited

U.S. PATENT DOCUMENTS 5,674,698 A * 10/1997 Zarling et al. ............. 435/7.92

FOREIGN PATENT DOCUMENTS

EP       0 947 823 A2    10/1999  .......... G01N/21/64

\* cited by examiner

Primary Examiner—F. L. Evans  
(74) Attorney, Agent, or Firm—Houston Eliseeva LLP

(57) ABSTRACT

An arrangement is proposed for detecting fluorescent light from a plurality of specimen points (2), in particular from microgene spots or microbiospots, the specimen points (2) being arranged on a slide (1). This arrangement comprises at least one light source for simultaneously illuminating the specimen points (2) with excitation light, and detection means, comprising detection elements (3), for simultaneously detecting the fluorescent light from the individual specimen points (2). According to the invention, the spacing d between the specimen points (2) and the respectively assigned detection elements (3) is selected to be as small as possible.

14 Claims, 4 Drawing Sheets

9

ARRANGEMENT FOR DETECTING FLUORESCENT LIGHT FROM A PLURALITY OF SAMPLE POINTS

CROSS REFERENCE TO RELATED APPLICATIONS

This application claims priority from a previously filed German application DE 100 03 754.2 filed on Jan. 28, 2000, which application is herein incorporated by reference.

BACKGROUND OF INVENTION

The invention relates to an arrangement for detecting fluorescent light from a plurality of specimen points, in particular from microgene spots or microbiospots, the specimen points being arranged on a slide, having at least one light source for simultaneously illuminating the specimen points with excitation light, and having detection means, comprising detection elements, for simultaneously detecting the fluorescent light from the individual specimen points.

Such arrangements are used, for example, for investigations in molecular biology or gene technology. The specimen to be investigated is mounted for this purpose on a slide and brought into contact with a fluorescing label. The substances present in the specimen and having an affinity with the label bind the label and can therefore be excited to emit fluorescent light. Conclusions on the composition of the specimen can therefore be drawn by detecting the fluorescent light emitted by a specimen.

European Patent Application EP 0 947 823 A2 describes a device for detecting a fluorescent dye in specimens, the individual specimen points being arranged on a slide. This slide is designed in the form of an optical conductor. Light is launched into the slide in order to excite the fluorescent dye at the individual specimen points. The fluorescent dye is then excited by the evanescent field formed at the interface between the slide and the specimen points. The known device can be used to detect simultaneously the fluorescent light from a series of specimen points, for which purpose, for example, a linear photodiode array, or else a CCD row is used as detection device. In addition to statistical investigations, in the case of which there is no need to assign the detected fluorescent radiation to a specific specimen point, the device described in EP 0 947 823 A2 also permits simultaneous individual investigations of a multiplicity of specimen points in the case of which the fluorescent light from each individual specimen point is detected with the capability of assignment. For this purpose, it is proposed to use a lens system with the aid of which the emitted fluorescent radiation of the individual specimen points can be focussed onto the device for detecting the fluorescent radiation.

In practice, both as regards design and with regard to the conduct of measurement, this measure turns out to be very expensive. Even, the implementation of a suitable lens system requires high precision in fabrication. In addition, the lens system not only has to be arranged, but also very precisely adjusted, between the slide, provided with specimen points, and the detection device, in order to achieve the desired focussing effect.

SUMMARY OF INVENTION

The present invention now proposes a very simple but extremely effective measure to prevent superimposition of the fluorescent light emitted by a plurality of specimen points at the location of a detection element, that is to say at the location of the measured value detection.

According to the invention, it is proposed for this purpose to select the spacing between the specimen points and the respectively assigned detection elements to be as small as possible so that the fluorescent light from the individual specimen points is detected in the manner of the production of a photographic contact print. Specifically, according to the invention it has been recognized that it is possible in this way to achieve very good results very easily.

In an advantageous way, the detection means could comprise a dedicated detection element for each specimen point. Depending on requirement, it would be possible as an alternative to this for each specimen point to be respectively assigned a plurality of detection elements. The respective application is the determining factor in this case.

In order to avoid superimposition of the fluorescent light from a plurality of specimen points at the location of a detection element, or of a plurality of respectively assigned detection elements, it is also possible to provide additional means within the scope of the present invention. In an advantageous variant, arranged for this purpose between the specimen points and the detection elements is at least one element which is transparent to fluorescent light emitted by a specimen point essentially in the direction of the assigned detection element, and totally reflects the fluorescent light emitted in the direction of adjacent specimen points, such that this fluorescent light is not detected. Such an element can be implemented, for example, in the form of a glass plate which is arranged between the specimen points and the detection elements, provided that the slide is likewise of plate-shaped design and the detection elements are arranged in a plane parallel to the slide and opposite the surface of the slide which is provided with the specimen points. The fluorescent light emitted at a steep angle by the specimen points in the direction of the detection elements can penetrate such a glass plate without hindrance, whereas the fluorescent light emitted in the direction of adjacent specimen points is totally reflected at the glass/air interface and deflected once more in the direction of the slide. By contrast with the lens system described in EP 0 947 823 A2, such a glass plate has the advantage that it need not be specially adjusted. Moreover, it is also less expensive to produce and maintain.

As a supplement, or also alternatively to the element described above, it is also possible effectively to suppress superimposition of the fluorescent light from a plurality of specimen points at the location of a detection element or a plurality of respectively assigned detection elements with the aid of mechanical, opaque barriers which are arranged between the specimen points and the detection elements such that they delimit detection channels for the individual specimen points and assigned detection elements.

As already mentioned, the detection means of the arrangement according to the invention comprise a dedicated detection element for each specimen point. In this context, the use of photodiode arrays or CCD chips has proved itself in practice.

The illumination of the specimen points with excitation light can also be implemented in various ways within the scope of the arrangement according to the invention for detecting fluorescent light from a plurality of specimen points. An advantageous variant is so-called transillumination. In this case, the slide is transparent at least to the excitation light. The light source is then arranged on the side of the slide averted from the specimen points such that the specimen points are illuminated through the slide. Another advantageous variant is total internal illumination by the slide. The slide is designed in this case in the form of an optical conductor. Moreover, means are provided for launching the light of the light source into the optical conductor such that the specimen points are illuminated by the evanescent field formed at the interface between slide and specimen points.

Finally, it may be mentioned further that in a particularly advantageous variant of the arrangement according to the invention for detecting fluorescent light from a plurality of specimen points, a filter arrangement which is essentially transparent only to the fluorescent light to be detected is also additionally arranged between the specimen points and the detection elements. In a simplest embodiment, such a filter arrangement could comprise only a blocking filter for the excitation light emitted by the light source, in order to suppress interference caused thereby when detecting the fluorescent light emitted by the specimen points. For the case in which the specimen points have been brought into contact with various labels before measurement, resulting in fluorescent light of different wavelengths being emitted by the specimens, it can also be sensible to equip such a filter arrangement with different filters for the fluorescent light of different wavelengths, in order to be able to detect different fluorescent dyes simultaneously, as an alternative.

BRIEF DESCRIPTION OF DRAWINGS

Advantageous refinements and developments of the invention are explained below with the aid of exemplary embodiments in conjunction with the figures, in which.

DETAILED DESCRIPTION

Figure 1:
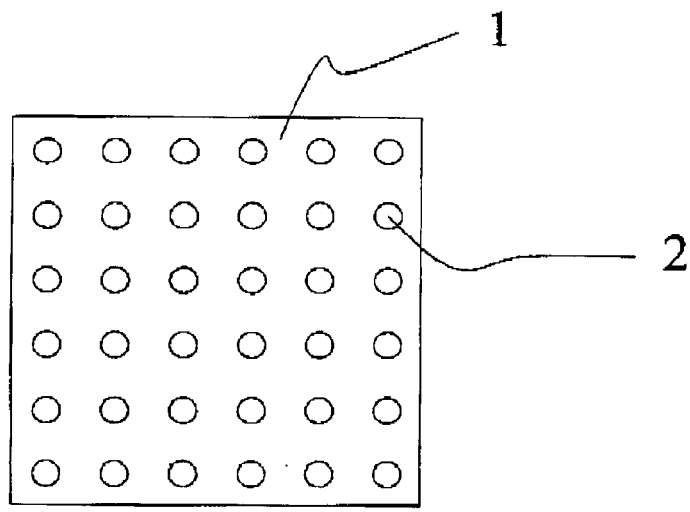
FIG. 1 shows the top view of a slide with specimen points.

Specimen points 2 are arranged in an array on the slide 1 illustrated in FIG. 1. The specimen points 2 are microspots whose diameters are approximately 10 to 100 μm.

The individual specimen points are brought into contact with a fluorescing label such that they emit fluorescent light in the case of illumination with corresponding excitation light.

A plurality of specimen points—here, all the specimen points 2 arranged on the slide 1—are illuminated simultaneously with excitation light with the aid of the arrangement according to the invention for detecting fluorescent light. The detection of the fluorescent light from the individual specimen points 2 is also performed simultaneously with the aid of the arrangement according to the invention, the detection means used therefor comprising a dedicated detection element for each specimen point.

Figure 2:
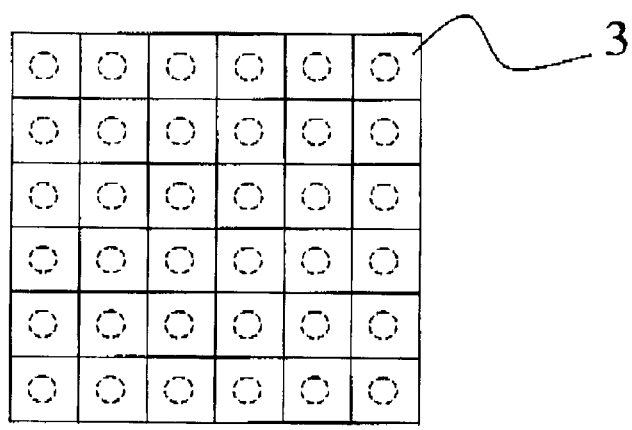
FIG. 2 shows the arrangement of a detection means over the slide illustrated in FIG. 1.

In the exemplary embodiment illustrated in FIG. 2, the simultaneous detection of the fluorescent light from the individual specimen points 2 is performed with the aid of a photodiode array which is arranged over the arrangement of the specimen points 2 on the slide 1 such that each specimen point 2 is covered by exactly one photodiode 3 of the photodiode array.

Since the fluorescent light emitted by the individual specimen points exhibits no preferred direction, spillover, that is to say superimposition of the fluorescent light emitted by the individual specimen points, can occur at the location of the detection elements. The fluorescent light detected by a detection element therefore need not have been emitted exclusively by the assigned specimen point. In order to suppress this spillover effect which falsifies the measurement results, it is proposed according to the invention to select the spacing between the specimen points and the respectively assigned detection elements to be as small as possible.

Figure 3:
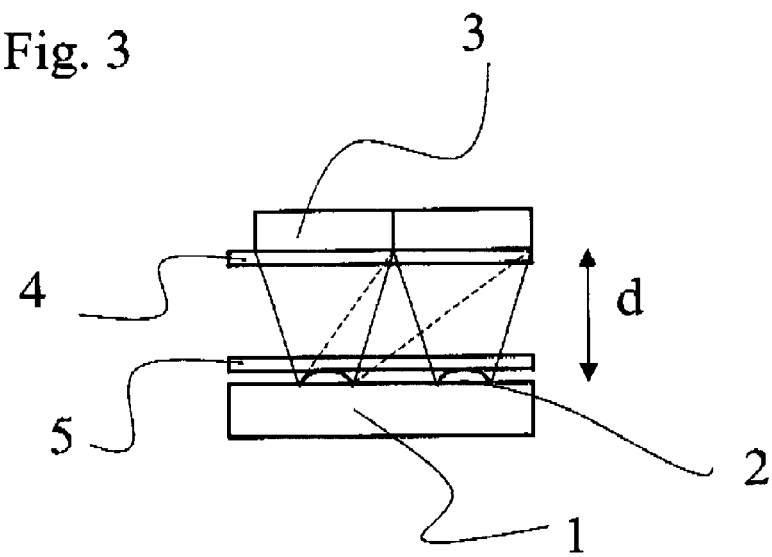
FIG. 3 shows the sectional illustration of an arrangement for detecting fluorescent light from a plurality of specimen points, in order to explain the beam path of the fluorescent light.

FIG. 3 illustrates the beam path of the fluorescent light emitted by a specimen point 2, and shows that the fraction of the fluorescent light emitted by a specimen point which is not detected by the detection element assigned to this specimen point becomes larger the larger the spacing d becomes between the specimen point and assigned detection element.

Figure 6:
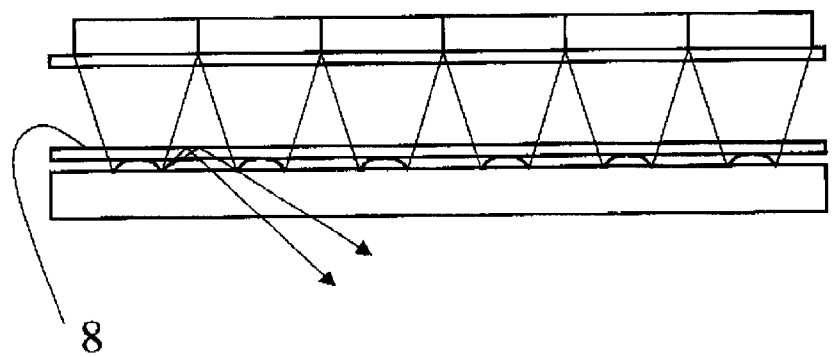
FIG. 6 shows the arrangement, illustrated in FIG. 3, for the purpose of explaining the beam path of the fluorescent light.

The specimen points 2 are covered in the arrangement illustrated in FIG. 3 by a cover glass 5 whose optical function is also explained in more detail in conjunction with FIG. 6. Furthermore, there is arranged between the specimen points 2 and the detection elements 3 a filter 4 which is essentially transparent only to the fluorescent light emitted by the specimen points, and serves, in particular, as blocking filter for the excitation light.

Figure 4:
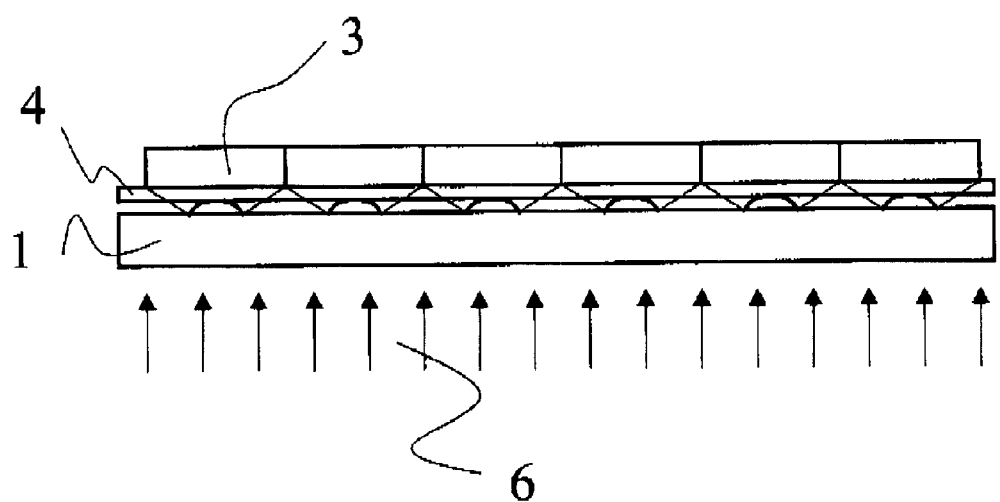
FIG. 4 shows the sectional illustration of an arrangement according to the invention with transillumination for the specimen points.

In the arrangement, illustrated in FIG. 4, for detecting the fluorescent light emitted by the specimen points 2 arranged on the slide 1, the spacing between the slide 1 or the specimen points 2 and the respectively assigned detection elements 3 is selected to be as small as possible by arranging the detection elements 3 directly over the specimen points 2, as it were. Only a filter 4, which serves as blocking filter for the excitation light, is interposed here. In the case illustrated in FIG. 4, the specimen points 2 are illuminated from below through the slide 1, which is transparent to the excitation light 6, for which reason the arrangement illustrated in FIG. 4 is also denoted as a transillumination arrangement.

Figure 5:
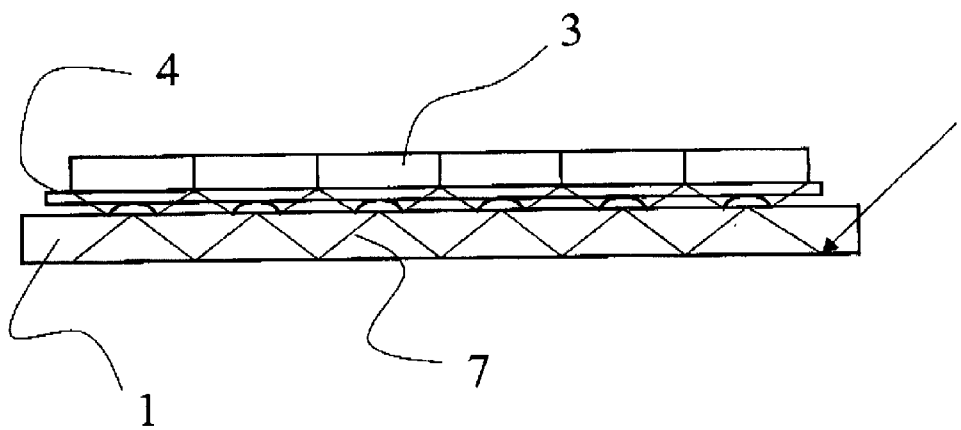
FIG. 5 shows the sectional illustration of an arrangement according to the invention with total internal illumination of the specimen points.

FIG. 5 shows a variant of the arrangement according to the invention with total internal illumination 7 of the specimen points 2. The slide 1 is designed here in the form of an optical conductor into which the light of a light source, for example a laser, is launched. The illumination of the specimen points 2 is performed here via the evanescent field which forms at the interface between slide 1 and specimen points 2. Here, once again, the detection elements 3 are also arranged with the filter 4 directly over the specimen points 2.

In addition to the filter 4 between the specimen points 2 and the detection elements 3, in the arrangement illustrated in FIG. 6 there is also arranged an element 8 which is in the form of a glass plate and additionally serves the purpose of suppressing superimposition of the fluorescent light from a plurality of specimen points 2 at the location of a detection element 3. FIG. 6 illustrates the beam path of the fluorescent light, emitted uniformly in the entire solid angle, from a specimen point 2, and the influence of the element 8 on this beam path. The fraction of the fluorescent light which is emitted by a specimen point 2 and is essentially emitted in the direction of the assigned detection element 3 and therefore strikes the glass plate 8 at an acute angle, penetrates the glass plate 8 essentially without hindrance and is detected by the detection element 3 which is assigned to the emitting specimen point 2. By contrast therewith, the fluorescent light emitted in the direction of adjacent specimen points and the associated detection elements is totally reflected at the glass plate 8, more precisely at the glass/air transition, such that this fraction of the fluorescent light is not detected by any detection element.

Figure 7:
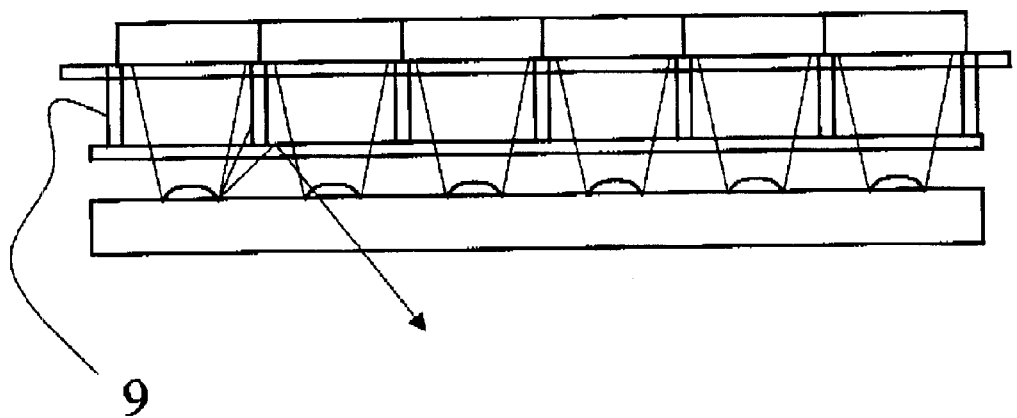
FIG. 7 shows a further arrangement according to the invention with mechanical barriers for the fluorescent light.

In addition to the glass plate 8, in the arrangement illustrated in FIG. 7 mechanical barriers 9 are also arranged between the individual specimen points 2 and the detection elements 3. These barriers 9 delimit detection channels for the individual specimen points 2 and the assigned detection elements 3, and in this way prevent superimposition of the fluorescent light from a plurality of specimen points 2 at the location of a detection element 3.

It may be pointed out again, in conclusion, that the invention is based on the idea of illuminating a plurality of specimen points simultaneously and using an appropriate number of detection elements such as, for example, a photodiode array or a CCD chip to detect them simultaneously, in a fashion analogous to a contact print in photography. This parallel read-out method is faster in principle than scanning methods.

A problem in this is the crosstalk in adjacent channels. It has been realized according to the invention that this crosstalk is less the more densely the detectors are applied to the specimen points.

Furthermore, crosstalk can be prevented when the light, which is emitted at a steep angle in the direction of an adjacent element, is totally reflected, for example at a glass/air interface. In addition, or else as a suplement thereto, mechanical barriers for avoiding crosstalk can be arranged between the individual detection elements.

What is claimed is:

1. An arrangement for detecting fluorescent light from a plurality of specimen points comprising:
    a slide bearing the plurality of specimen points, one light source for simultaneously illuminating the plurality of specimen points with excitation light,
    a plurality of detection elements, for simultaneously detecting the fluorescent light from the plurality of specimen points wherein a fraction of the fluorescent light emitted by a specimen point of the plurality of specimen points is detected only by a dedicated detection element of the plurality of detection elements; and
    a spacing (d) between the plurality of specimen points on the slide and the plurality of detection elements, wherein the spacing (d) is selected to be sufficiently small to allow only the dedicated detection element to detect the fraction of the fluorescent light emitted by the specimen point and avoid cross talk.

2. The arrangement according to claim 1, wherein each specimen point of the plurality of specimen points is respectively assigned each detector of the plurality of detection elements.

3. The arrangement according to claim 1, further providing means for avoiding superimposition of the fluorescent light front the plurality of specimen points at a location of the dedicated detection element.

4. The arrangement according to claim 3, wherein the means for avoiding are disposed at the location of a measured value.

5. The arrangement according to claim 1, further comprising at least one element disposed between the plurality of specimen points on the slide and the plurality of detection elements, at least one element being transparent to a the fraction of the fluorescent light emitted by the specimen point essentially in the direction of the dedicated detection element, and totally reflecting another fraction of the fluorescent light emitted in the direction of adjacent specimen points in order to avoid detection of is another fraction of the fluorescent light.

6. The arrangement according to claim 5, wherein at least one element is a glass plate.

7. The arrangement according to claim 1, further comprising a plurality of mechanical opaque barriers disposed between the plurality of specimen points on the slide and the plurality of detection elements, the plurality of barriers defining detection channels between individual specimen points and the plurality of detection elements serving to suppress superimposition of the fluorescent light from the plurality of specimen points at the location of the dedicated detection element or from the plurality of detection elements.

8. The arrangement according to claim 1, wherein the plurality of detection elements comprise at least one photodiode array.

9. The arrangement according to claim 1, wherein the plurality of detection elements comprise at least one CCD chip.

10. The arrangement according to claim 1, wherein the slide is transparent at least to the excitation light, wherein in that the light source is arranged on the side of the slide opposite from the plurality of specimen points and wherein the plurality of specimen points are illuminated through the slide.

11. The arrangement according to claim 1, further comprising means for launching the excitation light into the slide in form of an optical conductor, wherein the plurality of specimen points are illuminated by an evanescent field formed at the interface between the slide and the plurality of specimen points on the slide.

12. The arrangement according to claim 1, further comprising a filter arrangement which is transparent essentially only to the fluorescent light to be detected, the filter arrangement being disposed between the plurality of specimen points on the slide and the plurality of detection elements.

13. The arrangement of claim 1, wherein the plurality of specimen points comprise at least one microgene spot.

14. The arrangement of claim 1, wherein the plurality of specimen points comprise at least one microbiospot.

* * * * *